US00PP21984P2

(12) United States Plant Patent
Falstad

(10) Patent No.: US PP21,984 P2
(45) Date of Patent: Jun. 21, 2011

(54) ***HIBISCUS* PLANT NAMED 'CRANBERRY CRUSH'**

(50) Latin Name: ***Hibiscus hybrid* (L.)**
Varietal Denomination: Cranberry Crush

(75) Inventor: Clarence H. Falstad, Holland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 12/799,403

(22) Filed: Apr. 23, 2010

(51) Int. Cl.
*A01H 5/00* (2006.01)

(52) U.S. Cl. ..... Plt./257

(58) Field of Classification Search ..... Plt./257
See application file for complete search history.

*Primary Examiner* — Kent L Bell

(57) ABSTRACT

A new and distinct cultivar of hardy herbaceous *Hibiscus* hybrid plant named 'Cranberry Crush' comprising a naturally-short, compact, heavy-branching habit; also dark-green leaves with purple overtones and with a multitude of scarlet-red to dark-red slightly cupped flowers over at least 12 weeks during the summer until frost The new plant, *Hibiscus* 'Cranberry Crush' does not need to be pinched or sprayed with plant growth regulators to keep short and compact.

1 Drawing Sheet

Botanical classification: *Hibiscus* hybrid (L.).
Variety denomination: 'Cranberry Crush'.

BACKGROUND AND ORIGIN OF THE PLANT

The present invention relates to the new and distinct hardy, herbaceous, *hibiscus* plant, *Hibiscus* ' Cranberry Crush' hybridized by Clarence H. Falstad in the summer of 2006 at a nursery in Zeeland, Mich. The new plant, originally labeled # 06-87-02, is from a cross between the proprietary hybrid # 04-24-01 (not patented) (female pod parent) times the proprietary hybrid # 04-17-13 (not patented) (male pollen parent). Both parents have a complex mixture of species in them, most likely including the species: *moscheutos, coccineus, laevis.* *Hibiscus* ' Cranberry Crush' has been propagated both by stem cuttings and tissue culture at the same nursery in Zeeland, Mich. The resultant plants have been found to be stable and true to type. in successive generations of asexual reproduction.

BRIEF SUMMARY OF THE PLANT

*Hibiscus* 'Cranberry Crush' differs from its parents as well as all other hardy *hibiscus* known to the applicant in many traits. The foliage color of 'Cranberry Crush' is a dark green with burgundy tinting. The foliage shape of 'Cranberry Crush' is variable, depending on the time of year and position on the stem. Most leaves are hastate to palmatifid with some either young leaves or those on immature plants being ovate. The flowers of 'Cranberry Crush' are slightly cupped with shiny scarlet-red to dark-red petals. The most similar *hibiscus* to 'Cranberry Crush' is *Hibiscus* 'Robert Fleming' U.S. Plant Pat. No. 14,776. The new plant has a similar scarlet-red to dark-red flower color, but the new plant has more lustrous inner petal surface, is more densely branched and floriferous, and the foliage of the new plant has finer texture, more deeply cleft, is more lustrous, and less rugose than 'Robert Fleming'.

*Hibiscus* 'Cranberry Crush' is a unique hardy herbaceous *hibiscus* with the following combined traits:

1. Naturally short, rounded habit with dense heavy branching.

2. Many slightly-cupped flowers with lustrous scarlet-red to dark-red petals.
3. Fine textured foliage of dark green with purple overtones.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
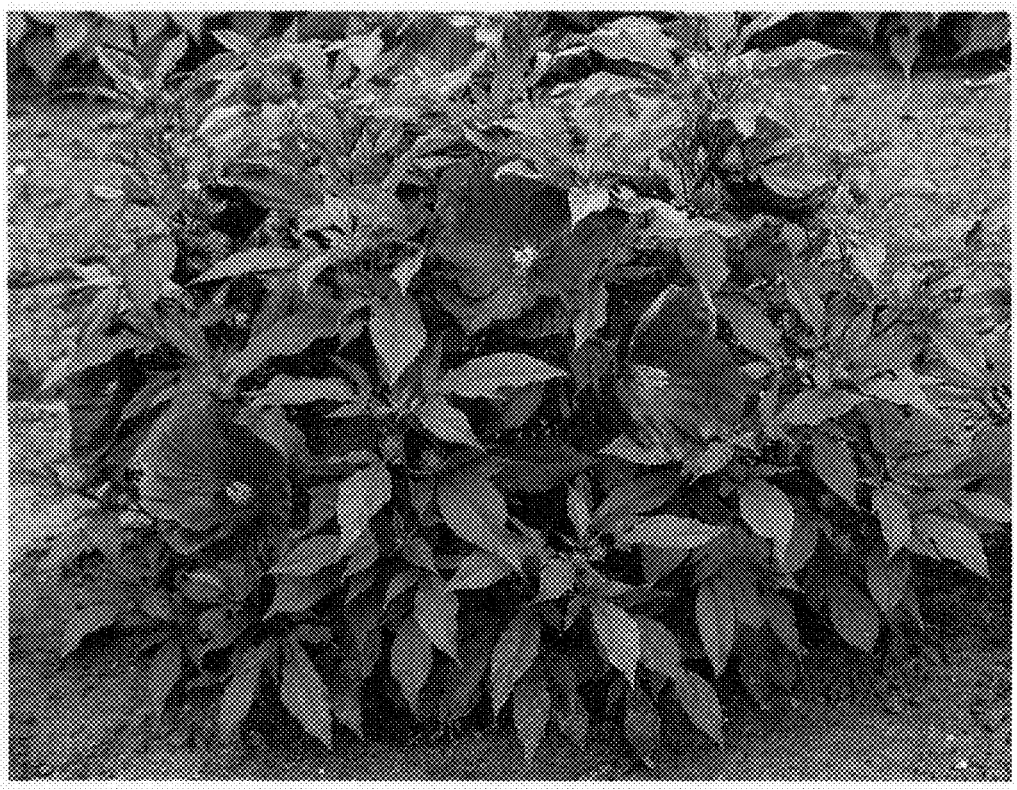
FIG. 1 shows the plant short, compact, rounded habit.
Figure 2:
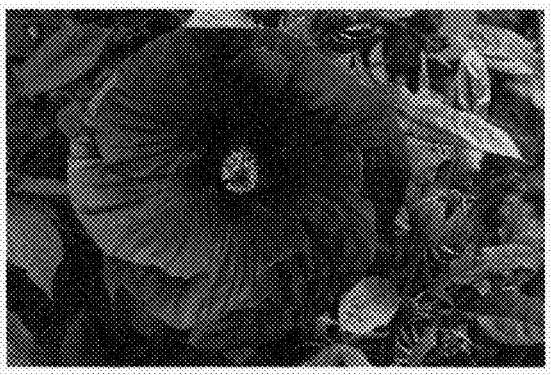
FIG. 2 shows a close-up of the flower with dark buds.

The following descriptions and color references are based on the 2001 edition of The Royal Horticultural Society Colour Chart except where common dictionary terms are used. The new plant, *Hibiscus* 'Cranberry Crush', has not been observed under all possible environments. The phenotype may vary slightly with different environmental conditions, such as temperature, light, fertility, moisture and maturity levels, but without any change in the genotype. The following observations and size descriptions are of two-year old and three-year old plants in the loamy-sand open field trials of a nursery in Zeeland, Mich. with supplemental fertilizer and water as needed. The plants are natural habit and were not treated with plant growth regulators, nor were they pinched at any time in the growth year.

Parentage: Proprietary hybrid # 04-24-01 (not patented) (female pod parent) times the proprietary hybrid # 04-17-13 (not patented) (male pollen parent)

Propagation:

*Method.*—Stem cuttings and sterile plant tissue culture division. Time to initiate roots from tissue culture: about two weeks.

*Rooting habit.*—Normal, branching, developing thick to about 4 cm diameter, fleshy; root color creamy white between RHS 159A and lighter than RHS 159 D depending on soil type.

*Crop time.*—Under normal summer growing conditions 12 to 18 weeks to flower in a four-liter container from cutting. Plant vigor is very good.

Plant description:

*Plant shape and habit.*—Hardy herbaceous perennial with 10 to 20 thick upright and heavily branched main stems producing a rounded mound; 8 to 15 primary branches per main stem protruding at 45° to 75° angle from vertical, secondary branches on the lower one third to half of the primary branches; lateral branch size: between 7.0 cm and 55 cm long (shorter at the upper nodes) and 0.4 cm to 1.2 cm diameter at the base of branch.

*Plant size.*—Unpinched plant with stems 80 to 100 cm tall, average about 95 cm tall from soil line, and diameter at base average about 2.5 cm; overall plant 100 to 120 cm wide at the base (widest point).

*Internode length.*—Unpinched plant varied between 3.0 to 7.0 cm, average about 5.0 cm.

*Foliage description.*—Opposite; dentate; glabrous; heterophyllous; base equilateral, hastate with lobes open to less than 90 degrees; shape hastate to palmatifid with some immature leaves oblong ovate with ovate bases and acute apexes, texture dull above and below with occasional leaf becoming lustrous; palmately veined; leaf size average 11 cm long and 5 cm wide, becoming smaller in distal portion of stem.

*Foliage color.*—Adaxial side between RHS 139A and RHS 139B with greyed-purple overtones of between RHS N187B and RHS N187A; abaxial side between RHS 147A and RHS 147B.

*Veins.*—Reticulate; primary and secondary adaxial veins becoming reddish between RHS 185A and. RHS 187D with greater light exposure and with less direct light nearest RHS 147C; primary abaxial veins between RHS 148C and RHS 148D, secondary veins the same color as surrounding leaf tissue on abaxial side.

*Petioles.*—Average size 5.0 cm long and 3.0 mm wide; mostly cylindrical with proximal petioles more plano-convex; color above nearest to RHS 183C, below between RHS 185D and RHS 185C.

Flower description:

*Buds.*—One day prior to opening about 5.5 cm long and 4.0 cm in diameter, acute apex and bluntly rounded base, unopened petals wrinkled at veins, exposed petal color nearest RHS N186B; prior to showing petals buds are about 3.5 cm long and 2.5 cm in diameter, Ovoid with acute apex, carinate at the fusion seam of the sepals; color between RHS 144A and RHS 145B with veining and sepal carina RHS 187C.

*Epicalyx.*—Entire, smooth, glabrous, linear with sharply acute apex, curved around sepals; 10 to 12 per flower; 2.5 cm long tapering to base of 4 mm wide; adaxial color RHS 144A, abaxial color RHS 144C occasional tinting of tips RHS 187C.

*Sepals.*—5, proximal half connate forming campanulate star-shaped calyx; acute apex; margin entire, edentate; about 4.5 cm long and 5.5 cm wide; abaxial color nearest RHS 144A and adaxial color nearest RHS 144C; five primary sepal veins nearly same color as sepal RHS 144D on inside and nearest RHS 183D on outside.

*Flowers.*—Solitary, 15 to 20 per main stem without pinching; slightly cupped petals opening to about 140 degrees; upward and outwardly facing; average 18 cm across and 8.5 cm deep; larger in early part of flowering season; persist for a one to two days; effective for at least 12 weeks beginning mid July and lasting into October; no detectable fragrance.

*Petals.*—Five; glabrous, slightly lustrous, adnate to the androecium, imbricate to about 120% overlapping at widest part (petals completely overlapping the next petal and 20% of the petal in the position two over); shape: rounded; margins: entire, edentate; apex: rounded; base: short claw-like; average 11 cm long and 13 cm wide at widest portion (larger in earlier part of flowering season); petal front color between RHS 45 and RHS 46A slightly darker eye of about RHS 185B measuring about 3.5 cm diameter; back color nearest RHS 46A; petal veins ribbed from apex nearly to base and same color as surrounding petal on front and back; petal veins deeply impressed to appear slightly ruffled.

*Gynoecium.*—Style enclosed in column that is average 6.5 cm long and 1.5 cm wide at base; column color nearest RHS N59C; distal 7 to 9 mm portion of style split into five branches and protrudes from column, branch diameter 2 mm, branch color nearest RHS 59B.

*Stigma.*—Five; globose, puberulose, about 3 mm in diameter, nearest RHS 59A; Ovary color: closest to RHS 145C.

*Androecium.*—Filaments: numerous, about 140; less than 1 mm in diameter and about 5 mm long; attached to nearly the entire length of column; nearest RHS N66D.

*Anthers.*—Reniform; about 2 mm long and 1 mm wide; nearest RHS 11D.

*Pollen.*—Numerous, globose, less than 0.1 mm long, nearest RHS 18B.

*Pedicel.*—From base of sepal to abscission point average 1.5 cm long and 4 mm wide on early flowers decreasing in distal flowers; color nearest RHS 183B with high light exposure and nearest RHS 138B with more shading.

*Peduncle.*—Flowers are easily visible held out average 5.5 cm long from abscission point to stem and 4 mm wide on early flowers shortening to about 5 cm higher on stem; color between RHS 183B and RHS 183C with light exposure and nearest 138B with more shading.

*Fruit.*—Few, loculicidal capsule; glabrous; globose, occasionally with abruptly acute apex; RHS N199B when mature.

*Seed.*—Minutely floccose, globose to slightly reniform; 3 to 4 mm in diameter; RHS 200A.

Disease resistance: Resistance beyond that of other hardy *hibiscus* cultivars has not been observed. The plant grows best with plenty of moisture and adequate drainage, but is able to tolerate some drought when mature.

Hardiness at least from USDA zone 4 through 9, and other disease resistance is typical of that of other *hibiscus* cultivars.

I claim:

1. A new cultivar of hardy herbaceous *Hibiscus* hybrid plant named 'Cranberry Crush' as herein illustrated and described, comprising a naturally-short, compact, heavy-branching habit; also dark-green leaves with purple overtones and with a multitude of scarlet-red to dark-red slightly cupped flowers over at least 12 weeks during the summer until frost suitable for potted plant culture, landscaping and especially in confined spaces because of the compact habit.

* * * * *

HIBISCUS PLANT NAMED 'CRANBERRY CRUSH'